(12) United States Patent
Nishida et al.

(10) Patent No.: US 6,187,568 B1
(45) Date of Patent: Feb. 13, 2001

(54) MACROCYCLIC LACTONE COMPOUNDS AND THEIR PRODUCTION PROCESS

(75) Inventors: Hiroyuki Nishida; Yuji Yamauchi; Taisuke Inagaki; Yasuhiro Kojima; Nakao Kojima, all of Taketoyo-cho (JP)

(73) Assignee: Pfizer Inc, New York, NY (US)

( * ) Notice: Under 35 U.S.C. 154(b), the term of this patent shall be extended for 0 days.

(21) Appl. No.: 09/378,062

(22) Filed: Aug. 20, 1999

Related U.S. Application Data

(63) Continuation of application No. 08/836,213, filed as application No. PCT/IB95/00870 on Oct. 13, 1995, now Pat. No. 6,001,998.

(30) Foreign Application Priority Data

Nov. 10, 1994 (JP) ........................................ PCT/JP94/01896

(51) Int. Cl.[7] ............................ C12P 17/18; A61K 35/00
(52) U.S. Cl. ............................................. 435/119; 424/115
(58) Field of Search .............................. 424/115; 435/119

(56) References Cited

U.S. PATENT DOCUMENTS 5,674,732 * 10/1997 Nishida et al. ........................ 435/119
6,001,998 * 12/1999 Nishida et al. ........................ 540/456

* cited by examiner

*Primary Examiner*—Herbert J. Lilling
(74) *Attorney, Agent, or Firm*—P. C. Richardson; P. H. Ginsburg

(57) ABSTRACT

This invention provides a process for producing a macrocyclic lactone compound, which comprises cultivating Actinoplanes sp. FERM BP-3832, in the presence of L-proline, L-hydroxyproline or L-nipecotic acid, and then isolating a macrocylic lactone compound from the fermentation broth. The compounds produced by this process include a compound of the following formula:

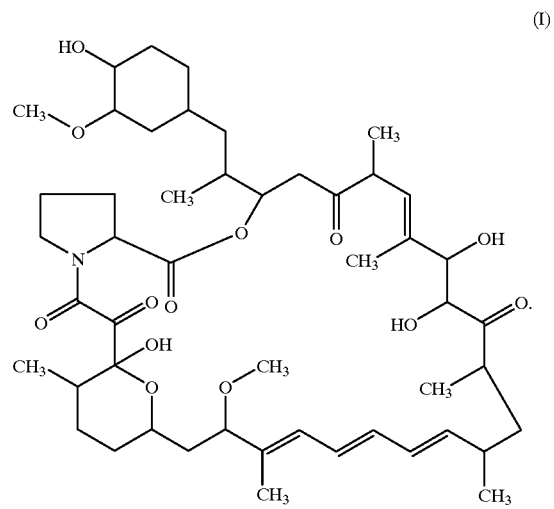

(I)

The present invention also relates to a pharmaceutical composition comprising the same, which is useful as immunosuppressive, antimycotic, antitumor agent or the like.

9 Claims, 7 Drawing Sheets

MACROCYCLIC LACTONE COMPOUNDS AND THEIR PRODUCTION PROCESS

This application is a continuation of Ser. No. 08/836,213 filed Oct. 27, 1997 now U.S. Pat. No. 6,001,998 which is a 371 of PCT/IB95/00870, filed Oct. 13, 1995.

TECHNICAL FIELD

This invention relates to a novel macrocyclic lactone compound, and particularly to a novel macrocyclic lactone compound produced by fermentation of a microorganism designated as Actinoplanes sp., which has been deposited as FERM BP-3832. This invention also relates to a process for producing the macrocyclic lactone compounds, and a pharmaceutical composition comprising the same, which is useful as immunosuppressive, antimycotic, antitumor agent or the like.

BACKGROUND ART

In 1983, the United States Food and Drug Administration approved cyclosporin for use in human subjects as an anti-rejection drug. Use of cyclosporin has revolutionized the filed of organ transplant surgery. The drug acts by the inhibition of the body's immune system from mobilizing its vast arsenal of natural protecting agents to reject the transplant's foreign protein. Although cyclosporin is effective in fighting transplantation rejection, it suffers drawbacks in causing kidney failure, liver damage and ulcers which in many cases can be very severe. Accordingly, safer drugs exhibiting less side effects have been investigated.

It was reported that some macrolide compounds, rapamycin and its analogs have immunosuppressive activity or the like (European Patent Publication No. 0184162; U.S. Pat. Nos. 3,929,992 and 3,993,749). European Patent Publication No. 0589703A discloses 21-norrapamycin useful in the treatment or prevention of transplantation rejection, autoimmune diseases and the like. Also, some rapamycin analogs having immunosuppressive activity are disclosed in Japanese Patent Application Laid-Open No. 292948/1993.

The object of the present invention is to provide a novel macrocyclic lactone compound having an excellent immunosuppressive, antimycotic or antitumor activity, and a pharmaceutical composition comprising the same.

Other objects of the present invention are to provide a process for producing the novel macrocyclic lactones, pharmaceutical compositions containing them and methods for using them.

BRIEF DISCLOSURE OF THE INVENTION

Accordingly, the present invention provides the macrocyclic lactone compound identified as CJ-12,798, which has the following chemical formula:

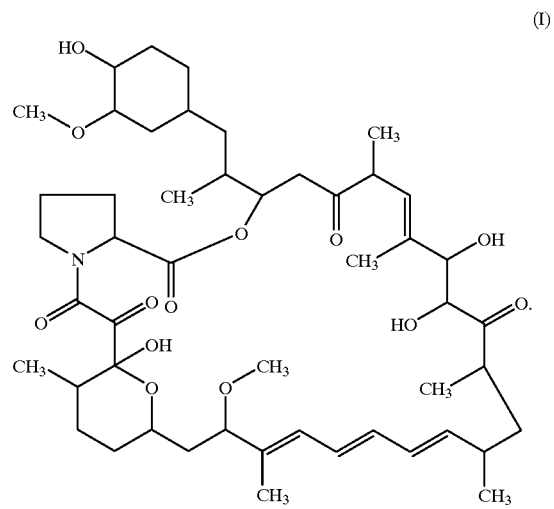

Additionally, this invention provides the macrocyclic lactone compounds designated as CJ-13,502; CJ-13,503 and CJ-13,504 having characteristics described below.

Further, the present invention provides a process for producing the macrocyclic lactone compounds, CJ-12,798, CJ-13,502, CJ-13,503 and CJ-13,504, which comprises cultivating a microorganism having the identifying characteristics of Actinoplanes sp. FERM BP-3832, or a mutant or recombinant form thereof, in the presence of L-proline, L-hydroxyproline or L-nipecotic acid.

Also, the present invention provides a pharmaceutical composition for use in the treatment or prevention of transplantation rejection, autoimmune diseases, mycotic diseases or tumors, which comprises a compound selected from CJ-12,798, CJ-13,502, CJ-13,503 and CJ-13,504, and a pharmaceutically acceptable carrier.

DETAILED DESCRIPTION OF THE INVENTION

Figure 1:
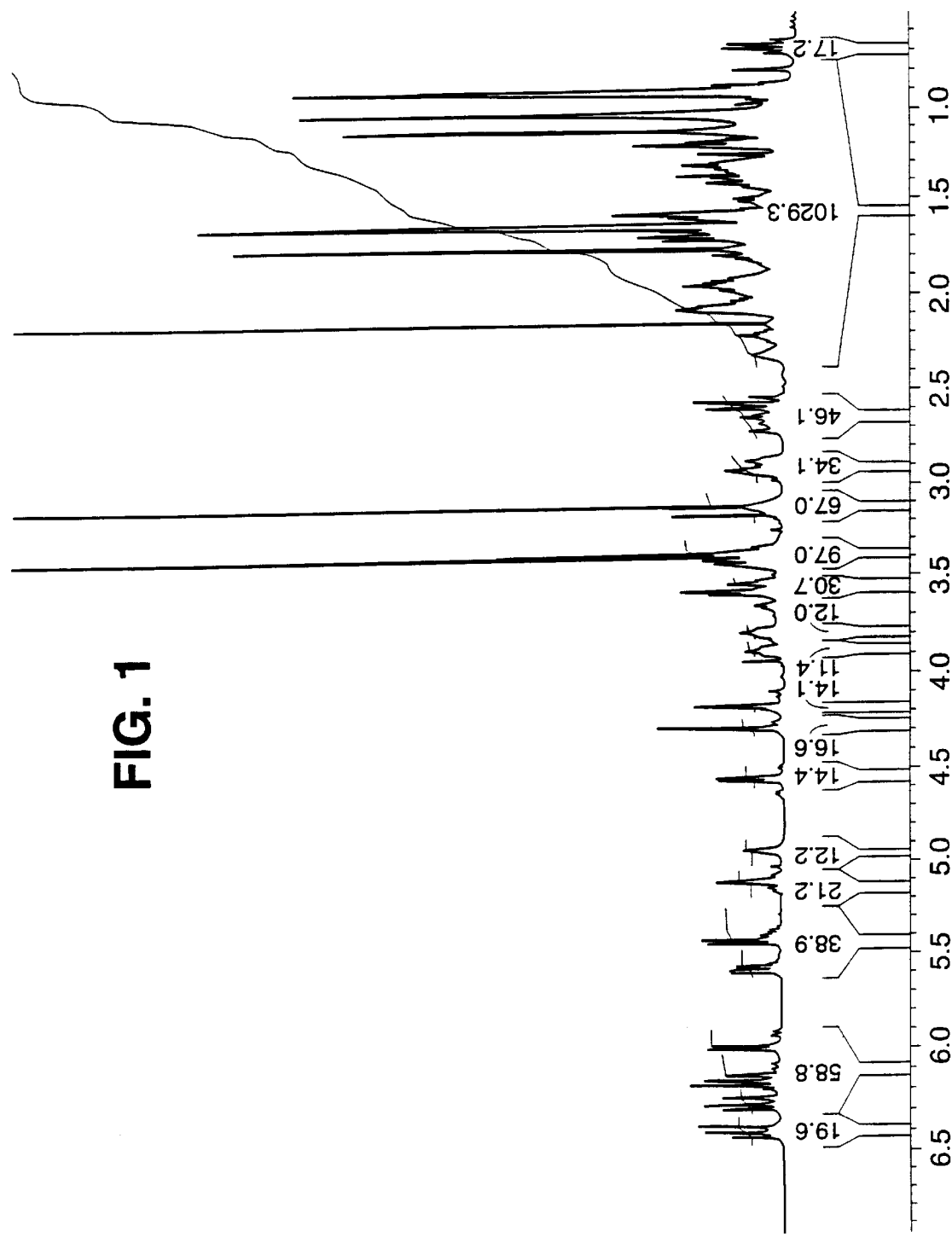
FIG. 1 is the $^1$H NMR spectrum of the compound of CJ-12,798.

The microorganism which is used in this invention is a strain of Actinoplanes sp. which was deposited as Actinoplanes sp. FERM BP-3832 at National Institute of Bioscience and Human-Technology, Agency of Industrial Science and Technology (located at 1-3, Higashi 1-chome, Tsukuba, Ibaraki, 305, Japan) under the Budapest Treaty on Apr. 13, 1992. The details of this strain, including its taxonomical properties, are described in Japanese Patent Application Laid-Open No. 304946/1993.

In this invention, a mutant or recombinant form of FERM BP-3832 having the ability to produce the macrocyclic lactone compounds, CJ-12,798, CJ-13,502, CJ-13,503 and CJ-13,504, can be also used. The mutant or recombinant form may be obtained by spontaneous mutation, artificial mutation with ultraviolet radiation or treatment with mutagen such as N-methyl-N-nitro-ninitrosoguanidine or ethyl methanesulfonate, or a cell technology method such as cell fusion, gene manipulation or the like, according to well-known methods.

According to the present invention, the macrocyclic lactone compounds of the invention may be produced by aerobic fermentation of FERM BP-3832, or a mutant or recombinant form thereof, under conditions similar to those generally employed to produce bioactive compounds by fermentation (e.g., as described in Japanese Patent Appln. Laid-Open No. 292948/1993), except that L-proline, L-hydroxyproline or L-nipecotic acid is added to the fermentation broth.

Cultivation of Actinoplanes sp. FERM BP-3832, or a mutant or recombinant form thereof, is usually conducted under submerged aerobic conditions with agitation at a temperature of 20 to 40° C. for 1 to 10 days, which may be varied according to fermentation conditions. Cultivation of FERM BP-3832 to produce said macrocyclic lactone compounds preferably takes place in aqueous nutrient media in the presence of L-proline, L-hydroxyproline or L-nipecotic acid at a temperature of 25 to 35° C. for 1 to 3 days. The L-proline or the like is added at a concentration of 0.1 to 1.0% (wt./vol.), preferably 0.4 to 0.6% (wt./vol.) to the fermentation broth. The pH of medium may be adjusted in the range of from 4.0 to 9.0, preferably from 6.0 to 7.5.

Nutrient media useful for fermentation include a source of assimilable carbon such as sugars, starches and glycerol; a source of organic nitrogen such as casein, enzymatic digest of casein, soybean meal, cotton seed meal, peanut meal, wheat gluten, soy flour, meat extract and fish meal; and a source of growth substances such as mineral salts, sodium chloride and calcium carbonate; and trace elements such as iron, magnesium, copper, zinc, cobalt and manganese. If excessive foaming is encountered during fermentation, antifoam agents such as polypropylene glycols or silicones may be added to the fermentation medium.

Aeration of the medium in fermentors for submerged growth is maintained at 3 to 200%, preferably at 50 to 150% volumes of sterile air per volume of the medium per minute. The rate of agitation depends on the type of agitator employed. A shake flask is usually run at 150 to 250 rpm whereas a fermentor is usually run at 300 to 2,000 rpm. Aseptic conditions must, of course, be maintained through the transfer of the organism and throughout its growth.

The macrocyclic lactone compounds thus produced may be isolated by standard techniques such as extraction and various chromatographic techniques.

The four macrocyclic lactone compounds, CJ-12,798, CJ-13,502, CJ-13,503 and CJ-13,504 were isolated from the fermentation broth, and examined by various spectroscopic techniques, as indicated in FIGS. 1 to 9, and HPLC analysis.

It is believed that CJ-12,798 has the following stereo-structure.

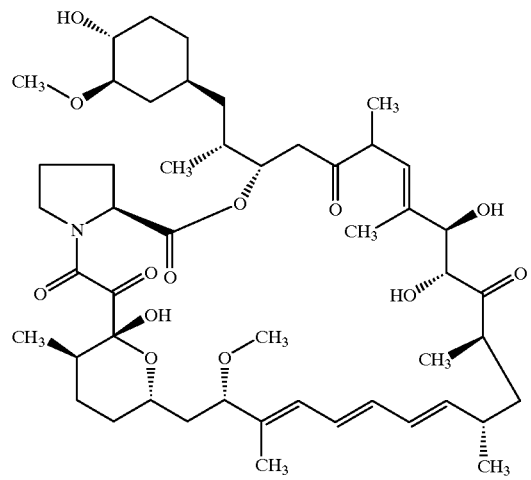

Figure 2:
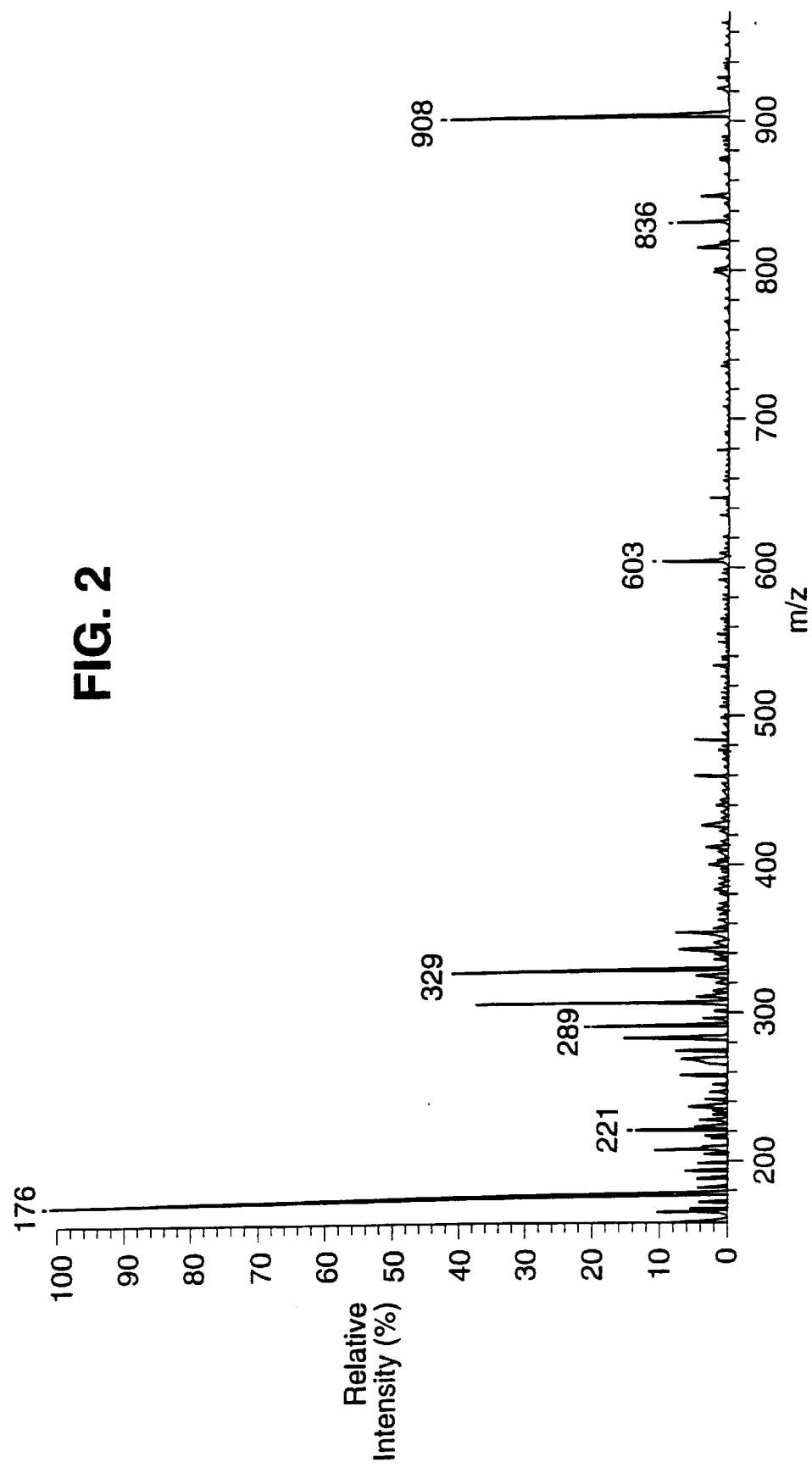
FIG. 2 is the LSI mass spectrum of the compound CJ-12,798.
Figure 6:
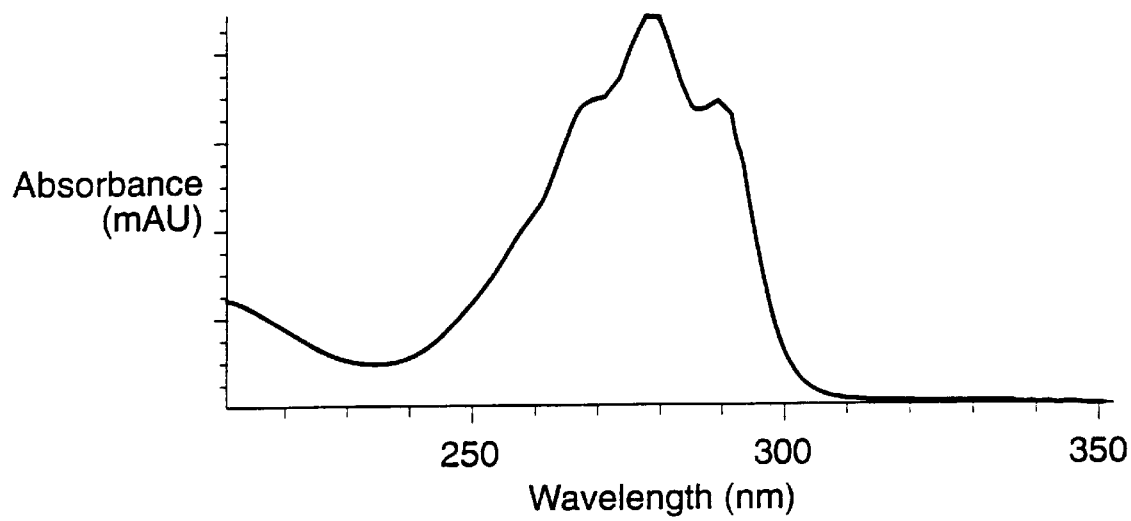
FIG. 6 is the UV spectrum of the compound CJ-12,798.

Further, compound CJ-12,798 has the characteristic LSI mass spectrum shown in FIG. 2, with m/z 908 [M+Na]+; the UV spectrum shown in FIG. 6, with a UV max at 267, 277 and 287 nm in methanol; and a retention time of 12.9 min on HPLC using a Pegasil (Senshu's trademark) ODS column (4.6×150 mm) and eluting with methanol-water (7:3 to 10:0) for 30 min at a flow rate of 0.7 ml/min at 42° C.

Figure 3:
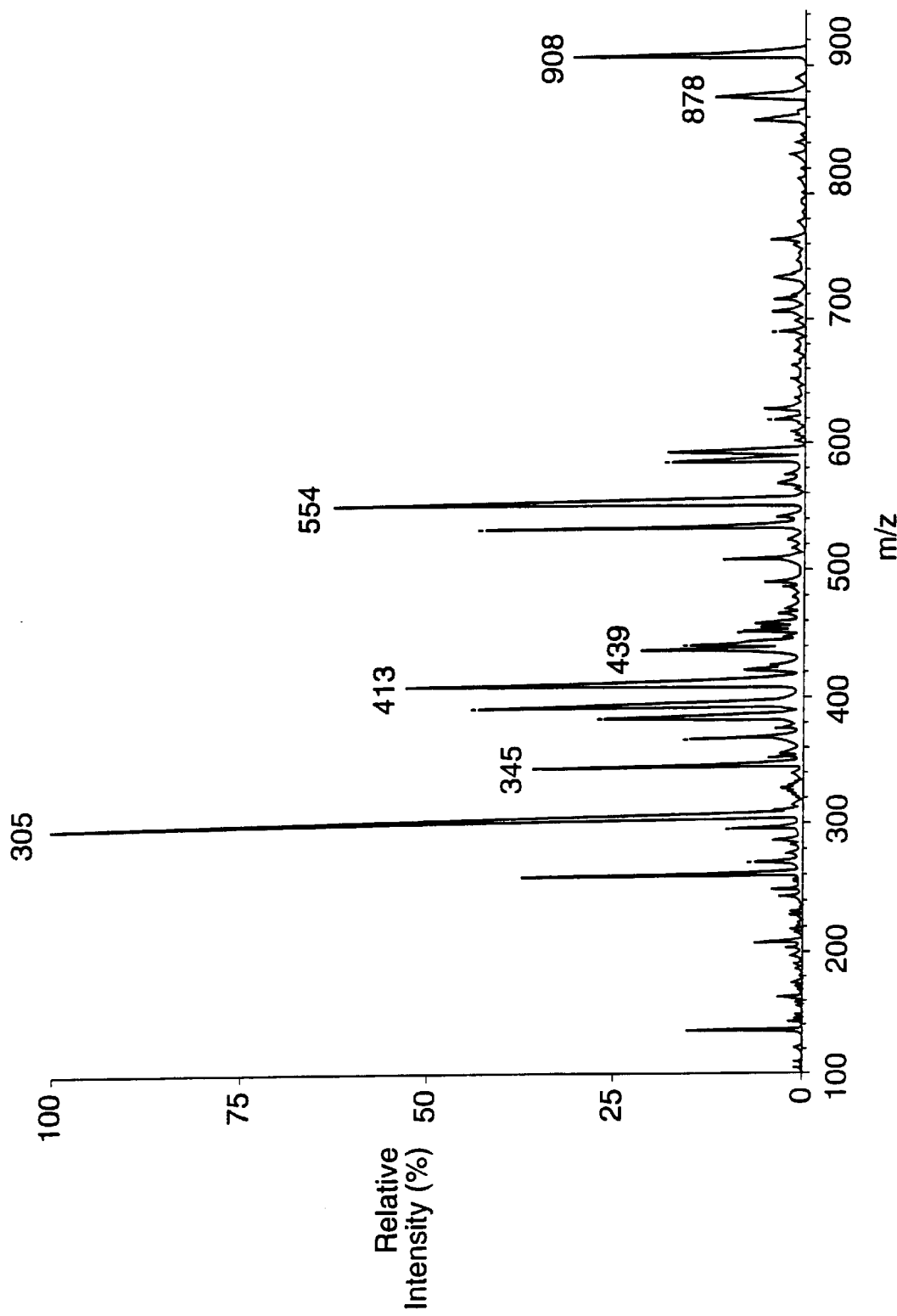
FIG. 3 is the ESI mass spectrum of the compound CJ-13,502.
Figure 7:
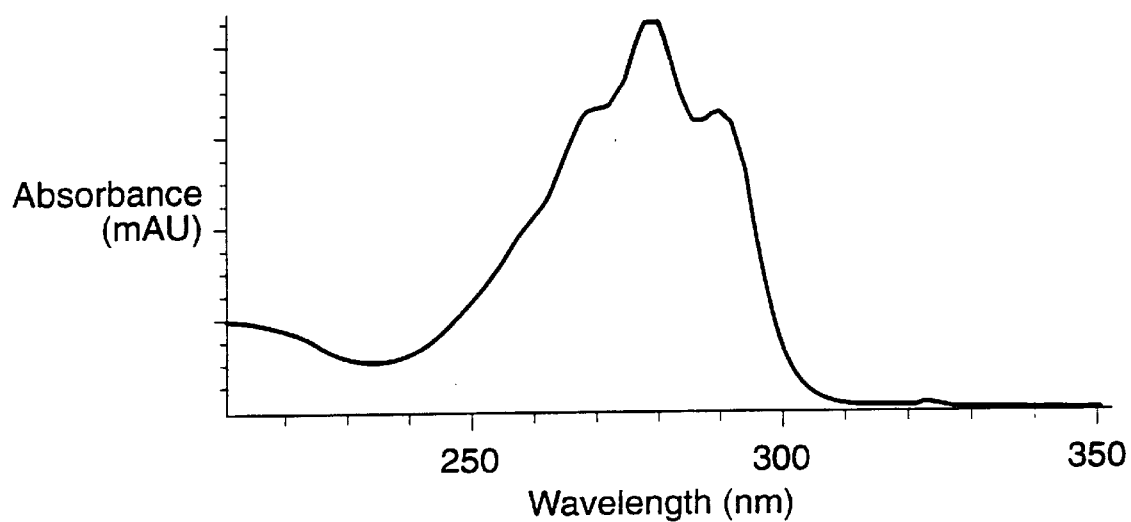
FIG. 7 is the UV spectrum of the compound CJ-13,502.

Compound said CJ-13,502 has the characteristic ESI mass spectrum shown in FIG. 3, with m/z 908 [M+Na]+; the UV spectrum shown in FIG. 7, with a UV max at 267, 277 and 288 nm in methanol; and a retention time of 12.8 min on HPLC using a Pegasil (Senshu's trademark) ODS column (4.6×150 mm) and eluting with methanol-water (7:3 to 10:0) for 30 min at a flow rate of 0.7 ml/min at 42° C.

Figure 4:
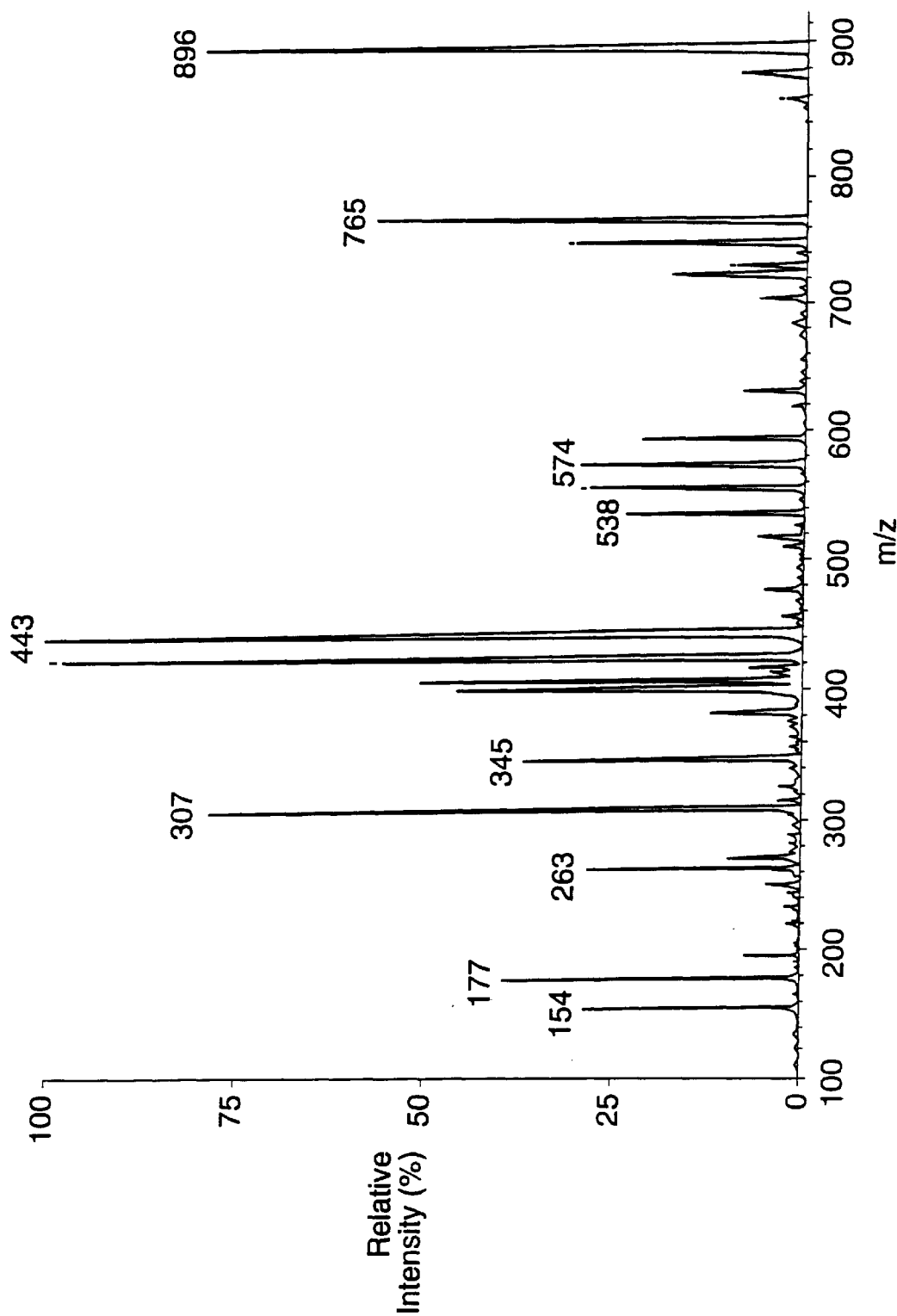
FIG. 4 is the ESI mass spectrum of the compound CJ-13,503.
Figure 8:
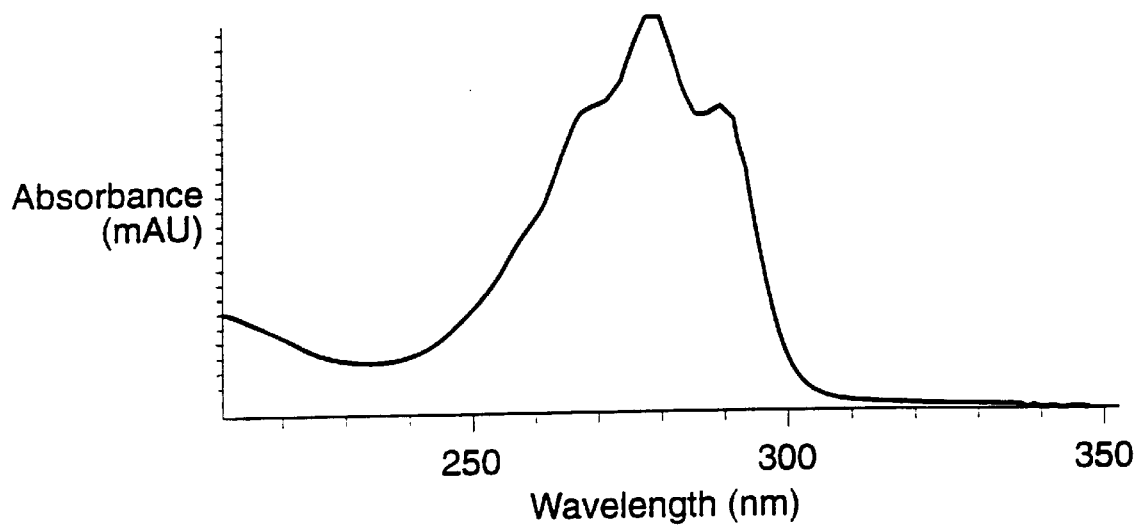
FIG. 8 is the UV spectrum of the compound CJ-13,503.

Compound CJ-13,503 has the characteristic ESI mass spectrum shown in FIG. 4, with m/z 896 [M+Na]+ in ESI mass spectrum; the UV spectrum shown in FIG. 8, with a UV max at 267, 277 and 288 nm in methanol; and a retention time of 10.9 min on HPLC using a Pegasil (Senshu's trademark) ODS column (4.6×150 mm) and eluting with methanol-water (7:3 to 10:0) for 30 min at a flow rate of 0.7 ml/min at 42° C.

Figure 5:
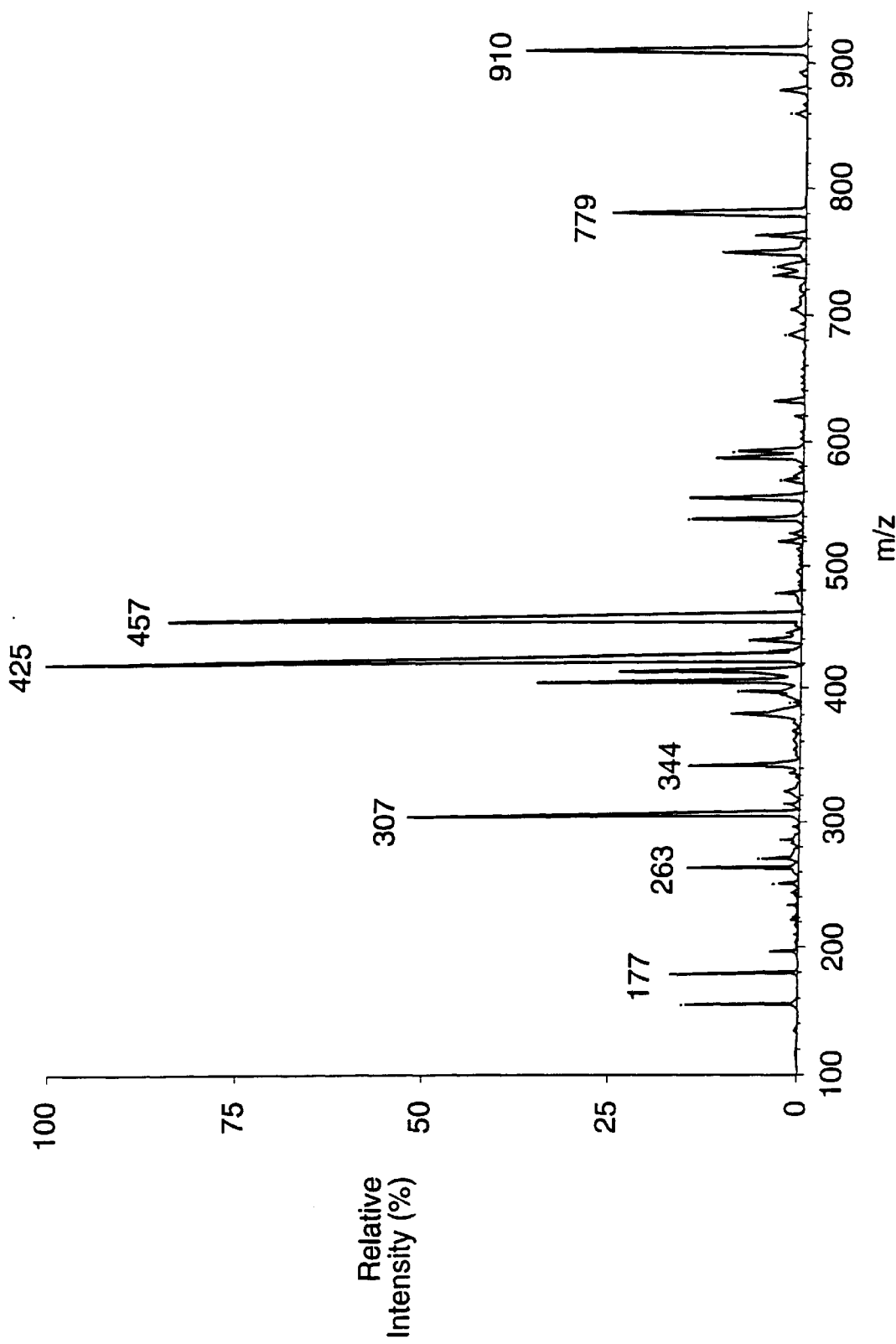
FIG. 5 is the ESI mass spectrum of the compound CJ-13,504.
Figure 9:
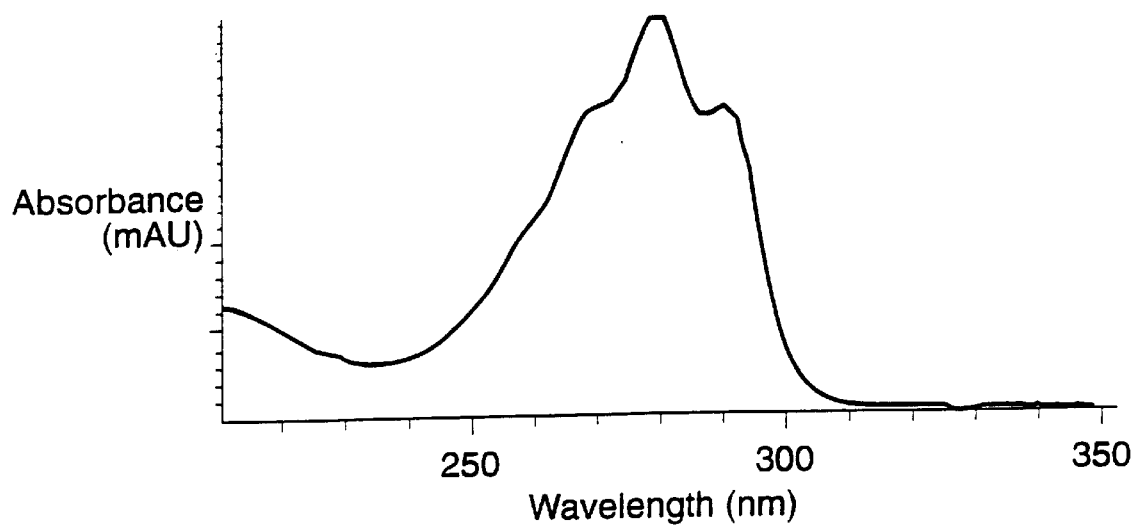
FIG. 9 is the UV spectrum of the compound CJ-13,504.

Compound CJ-13,504 the characteristic ESI mass spectrum shown in FIG. 5, with m/z 910 [M+Na]+; the UV spectrum shown in FIG. 9, with a UV max at 267, 277 and 288 nm in methanol; and a retention time of 11.9 min on HPLC using a Pegasil (Senshu's trademark) ODS column (4.6×150 mm) and eluting with methanol-water (7:3 to 10:0) for 30 min at a flow rate of 0.7 ml/min at 42° C.

The immunosuppressive properties of the macrocyclic lactone compound of formula (I) and the other compounds produced by the process of this invention, were demonstrated by measuring their human mixed lymphocyte reaction (MLR) inhibitory activities. The measurement of the human MLR activity of the macrocyclic lactone compounds of this invention was carried out by standard procedures which are described in the literature (D. P. Dubey et al., in Manual of Clinical Laboratory Immunology, 3rd Ed., pp. 847–858, 1986). Cytotoxicities were measured by standard procedure (T. Mosmann, J., J. Immunol. Methods, 65:55–63, 1983).

The compounds CJ-12,798, CJ-13,502, CJ-13,503 and CJ-12,504 showed MLR inhibitory activities ($IC_{50}$ values) which were more than one hundred times stronger than their cytotoxic activities. Out of these novel macrocyclic lactones, compound CJ-12,798 showed the highest immunosuppressive activity.

The antifungal activities of the compounds of the present invention were determined by a paper disk (8 mm, Advantec) method (agar plate medium: Antibiotic Medium 11 (Difco); test organism: *Candida albicans*). The macrocyclic lactone compounds CJ-12,798, CJ-13,502, CJ-13,503 and CJ-13,504 showed good antifungal activities, with CJ-12,798 showing the highest activity.

For use as an immunosuppressant, antimycotic or antitumor agent in a mammalian subject, especially a human subject, the macrocyclic lactone compounds of the present invention can be administered either alone, or with an inert carrier in a pharmaceutical composition, according to standard pharmaceutical practice. The macrocyclic lactone compounds can be applied by parenteral or oral administration. The active ingredient may be compounded, for example, with the usual non-toxic, pharmaceutically acceptable carriers for tablets, pellets, capsules, suppositories, solutions, emulsions, suspensions and other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations. In addition, if needed, auxiliary, stabilizing and coloring agents and perfumes may be used. In general, the macrocyclic lactone compounds of this invention may be present in such dosage forms at concentration levels ranging 5 to 70% by weight, preferably 10 to 50% by weight.

The macrocyclic lactone compounds of this invention can be used in mammalian subjects as immunosuppressive, antimycotic or antitumor agents in dosages ranging from 0.01 to 20 mg/kg. The dosage to be used in a particular case will vary according to a number of factors, such as the disease state or condition being treated, the potency of the individual compound being administered, the response of the particular subject and the route of administration. However, when a macrocyclic lactone compound of formula (I) is used in a human patient to treat or prevent transplantation rejection, the usual oral or parenteral dose will be from 0.5 to 250 mg/kg, and preferably 5 to 250 mg/kg, one to four times per day.

EXAMPLES

The present invention is illustrated by the following examples. However, it should be understood that the invention is not limited to the specific details of these examples. UV spectra were recorded in methanol on a JASCO Ubest-30 UV/VIS spectrophotometer. The NMR spectrum was measured in $CDCl_3$ by a Bruker NMR spectrometer (AM-500) unless otherwise indicated and peak positions are expressed in parts per million (ppm) based on the internal standard of $CDCl_3$ peak at 7.25 ppm. The peak shapes are denoted as follows: s, singlet; d, doublet; t, triplet; q, quartet; m, multiplet; br, broad. LSI (Liquid Secondary Ion) and ESI (electrospray Ion) mass spectra were measured by Kratos mass spectrometer (model 1S) using NaI-matrix of dithiothreitol: dithioerythritol (3:1) and Sciex mass spectrometer (model API III) using ammonium acetate matrix.

Example 1

One hundred (100) ml of Medium-1 (glucose 2%, Polypepton 0.5%, beef extract 0.3%, wheat gluten 0.5%, yeast extract 0.5%, blood meal 0.3% and $CaCO_3$ 0.4%, PH 7.0–7.2) in a 500 ml flask was inoculated with a vegitative cell suspension from a slant culture of Actinoplanes sp. FERM BP-3832. The flask was shaken at 28° C. for 3 days on a rotary shaker with 7-cm throw at 220 rpm, to obtain a first seed culture.

A shake flask containing Medium-1 (150 ml) was inoculated with 7.5 ml of the first seed culture. The flask was shaken at 28° C. for 2 days on the rotary shaker, to obtain a second seed culture.

The second seed culture was used to inoculate a 6-liter (L) fermentation vessel containing 3 L of sterile medium (Medium-2: glucose 2%, Polypepton 0.5%, beef extract 0.3%, yeast extract 0.5% and $CaCO_3$ 0.4%, PH 7.2–7.4). Aeration was carried out at 26° C. for 2 days with 1,700 rpm at 3 L per min, to obtain a third seed culture.

The third seed culture in the 6-L fermentation vessel was centrifuged for 10 min at 3,000 rpm and resuspended back to the original volume in a sterile medium (Medium-3: glucose 2.5%, MES 2.5%, PH 7.2–7.4). Aeration was carried out at 26° C. for 6 hours with 1,700 rpm at 3 L per min. Fifteen grams of L-proline (final concentration, 0.5%) was added to the fermentation broth and aeration was carried out at 26° C. for 3 days with 1,700 rpm at 3 L per min.

The fermentation broth (3 L) was filtered after the addition of 2 L of MeOH. The filtrate was then applied to a resin (Diaion HP20) (500 ml) and macrocyclic lactones were eluted with 2 L of acetone. The acetone eluate was concentrated to aqueous solution (1 L) and extracted three times with 1 L of ethyl acetate. The extract was dried over anhydrous $Na_2SO_4$ and evaporated to afford the oily residue (10.4 g). The oily residue (10 g) was applied to a Chemcosorb (Chemco's trademark) 5ODS-UH column (20×250 mm) and eluted with methanol-water (8:2) at flow rate of 5 ml/min. Detection was made by UV absorbance at 305 nm. The eluted peak was collected to yield the CJ-12,798 (1.0 mg). The compound was detected by HPLC using the Pegasil (Senshu's trademark) ODS column (4.6×150 mm) and eluting with methanol-water (7:3 to 10:0) for 30 min at flow rate of 0.7 ml/min at 42° C. The retention time of compound CJ-12,798 was 12.9 min (as compared to 15.2 min for rapamycin). The detection was carried out by UV at 280 nm.

In addition, the physicochemical properties of CJ-12,798 were determined as follows.

| | CJ-12,798 |
|---|---|
| Appearance | White powder |
| UVλmax (MeOH) | 267, 277, 288 |
| Molecular weight | 908 |
| Molecular formula | $C_{49}H_{75}NO_{13}$ |
| LSIMS m/z | 908.5 $[M + Na]^+$ |
| $^1$H NMR (ppm) | 3.14 (3H, s, –OMe), |
| | 3.41 (3H, s, –OMe) |

Example 2

The procedure similar to that of Example 1 was repeated except that the amino acid fed was changed from L-proline to L-hydroxyproline, and that Medium-2 was replaced by Medium-2A (glucose 3%, corn starch 1%, Pharmamedia 0.5%, Sungrowth 0.5%, corn steep liquor 0.75%, $CoCl_2.6H_2O$ 0.0001% and $CaCO_3$ 0.4%, PH 7.2–7.4).

As a result, the eluted peaks were collected to yield compounds CJ-13,503 (1.0 mg) and CJ-13,504 (1.5 mg). The compounds were detected by HPLC using the Pegasil (Senshu's trademark) ODS column (4.6×150 mm) and eluting with methanol-water (7:3 to 10:0) for 30 min at flow rate of 0.7 ml/min at 42° C. The retention times of compound CJ-13,503 and compound CJ-13,504 were 10.9 and 11.9 min, respectively. The detection was carried out by UV at 280 nm.

In addition, the physicochemical properties of CJ-13,503 and CJ-13,504 were determined as follows.

|  | CJ-13,503 | CJ-13,504 |
|---|---|---|
| Appearance | White powder | White powder |
| UVλmax (MeOH)(nm) | 267, 277, 288 | 267, 277, 288 |
| Molecular weight | 896 | 910 |
| ESIMS m/z | 896.5 [M + Na]$^+$ | 910.5 [M + Na]$^+$ |

Example 3

The procedure similar to that of Example 2 was repeated except that the amino acid fed was changed from L-hydroxyproline to L-nipecotic acid.

As a result, the eluted peak was collected to yield compound CJ-13,502 (1.0 mg). The compound was detected by HPLC using the Pegasil (Senshu's trademark) ODS column (4.6×150 mm) and eluting with methanol-water (7:3 to 10:0) for 30 min at flow rate of 0.7 ml/min at 42° C. The retention time of compound CJ-13,502 was 12.8 min. The detection was carried out by UV at 280 nm.

In addition, the physicochemical properties of CJ-13,502 were determined as follows.

|  | CJ-13,502 |
|---|---|
| Appearance | White powder |
| UVλmax (MeOH)(nm) | 267, 277, 288 |
| Molecular weight | 908 |
| ESIMS m/z | 908.5 [M + Na]$^+$ |

What is claimed is:

1. A macrocyclic lactone compound designated CJ-13,502, made by cultivating a microorganism having the identifying characteristics of Actinoplanes sp. FERM BP-3832, or a mutant or recombinant form thereof, in the presence of L-proline, L-hydroxyproline or L-nipecotic acid, and having the characteristics of ESI mass spectrum shown in FIG. 3, with m/z 908 [M+Na]+; the UV spectrum shown in FIG. 7, with a UV max at 267, 277 and 288 nm in methanol; and a retention time of 12.8 min. on HPLC using a Pegasil ODS column (4.6×150 mm) and eluting with methanol-water (7:3 to 10:0) for 30 min at a flow rate of 0.7 ml/min at 42° C.

2. A macrocylic lactone compound designated CJ-13,503, made by cultivating a microorganism having the identifying characteristics of Actinoplanes sp. FERM BP-3832, or a mutant or recombinant form thereof, in the presence of L-proline, L-hydroxyproline or L-nipecotic acid, and having the characteristics of ESI mass spectrum shown in FIG. 4, with m/z 896 [M+Na]+; the UV spectrum shown in FIG. 8, with a UV max at 267, 277 and 288 nm in methanol; and a retention time of 10.9 min. on HPLC using a Pegasil ODS column (4.6×150 mm) and eluting with methanol-water (7:3 to 10:0) for 30 min at a flow rate of 0.7 ml/min at 42° C.

3. A macrocyclic lactone compound designated CJ-13,504, made by cultivating a microorganism having the identifying characteristics of Actinoplanes sp. FERM BP-3832, or a mutant or recombinant form thereof, in the presence of L-proline, L-hydroxyproline or L-nipecotic acid, and having the characteristics of ESI mass spectrum shown in FIG. 5, with m/z 908 [M+Na]+; the UV spectrum shown in FIG. 9, with a UV max at 267, 277 and 288 nm in methanol; and a retention time of 11.9 min. on HPLC using a Pegasil ODS column (4.6×150 mm) and eluting with methanol-water (7:3 to 10:0) for 30 min at a flow rate of 0.7 ml/min at 42° C.

4. A pharmaceutical composition for use in the treatment or prevention of transplantation rejection, autoimmune diseases, mycotic diseases or tumors, which composition comprises a compound according to claim 2, and a pharmaceutically acceptable carrier.

5. A pharmaceutical composition for use in the treatment or prevention of transplantation rejection, autoimmune diseases, mycotic diseases or tumors, which composition comprises a compound according to claim 3, and a pharmaceutically acceptable carrier.

6. A process for producing the macrocyclic lactone compound claims 1, 2 or 3, which comprises cultivating a microorganism having the identifying characteristics of Actinoplanes sp. FERM BP-3832, or a mutant or recombinant form thereof, in the presence of L-proline, L-hydroxyproline or L-nipecotic acid.

7. The process according to claim 6, which further comprises the subsequent step of isolating said macrocyclic lactone compound from the fermentation broth.

8. A process according to claim 6, wherein the cultivation is carried out in the presence of L-proline.

9. A pharmaceutical composition for use in the treatment or prevention of transplantation rejection, autoimmune diseases, mycotic diseases or tumors, which comprises a compound according to claim 1, and a pharmaceutically acceptable carrier.

* * * * *